United States Patent
Sakaida et al.

(10) Patent No.: US 10,684,546 B2
(45) Date of Patent: Jun. 16, 2020

(54) COMPOSITION FOR FORMING RESIST UNDERLAYER FILM

(71) Applicant: NISSAN CHEMICAL CORPORATION, Tokyo (JP)

(72) Inventors: Yasushi Sakaida, Toyama (JP); Kenji Takase, Funabashi (JP); Takahiro Kishioka, Toyama (JP); Rikimaru Sakamoto, Toyama (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 16/097,586

(22) PCT Filed: Apr. 11, 2017

(86) PCT No.: PCT/JP2017/014849
§ 371 (c)(1),
(2) Date: Oct. 29, 2018

(87) PCT Pub. No.: WO2017/187969
PCT Pub. Date: Nov. 2, 2017

(65) Prior Publication Data
US 2019/0163063 A1 May 30, 2019

(30) Foreign Application Priority Data

Apr. 28, 2016 (JP) .................. 2016-091527

(51) Int. Cl.
| | | |
|---|---|---|
| G03F 7/11 | (2006.01) | |
| G03F 7/09 | (2006.01) | |
| C07D 487/04 | (2006.01) | |
| C09D 133/14 | (2006.01) | |
| C09D 163/00 | (2006.01) | |
| C08K 5/3445 | (2006.01) | |

(52) U.S. Cl.
CPC .............. *G03F 7/11* (2013.01); *C07D 487/04* (2013.01); *C09D 133/14* (2013.01); *C09D 163/00* (2013.01); *G03F 7/091* (2013.01); *C08K 5/3445* (2013.01)

(58) Field of Classification Search
None
See application file for complete search history.

(56) References Cited

U.S. PATENT DOCUMENTS

2004/0259019 A1* 12/2004 Yahagi .................. G03F 7/0226
430/154

FOREIGN PATENT DOCUMENTS

| CN | 105085532 | * | 7/2017 |
|---|---|---|---|
| JP | S55-142780 A | | 11/1980 |
| JP | H10-282653 A | | 10/1998 |
| JP | H11-160860 A | | 6/1999 |
| JP | 2007-84502 | * | 4/2007 |
| JP | 2015-051972 A | | 3/2015 |
| WO | 2008/143302 A1 | | 11/2008 |
| WO | 2009/096340 A1 | | 8/2009 |
| WO | 2010/055852 A1 | | 5/2010 |
| WO | 2015/046149 A1 | | 4/2015 |

OTHER PUBLICATIONS

Machine Translation of Hirosaki et al. JP 2007-84502 (Year: 2007).*
Machine Translation of Zhao et al. CN105085532 (Year: 2017).*
Jul. 4, 2017 International Search Report issued in International Patent Application No. PCT/JP2017/014849.
Jul. 4, 2017 Written Opinion of the International Searching Authority issued in International Patent Application No. PCT/JP2017/014849.

* cited by examiner

*Primary Examiner* — Robert T Butcher
(74) *Attorney, Agent, or Firm* — Oliff PLC (57) ABSTRACT

A composition for forming a resist underlayer film has excellent storage stability at normal temperature. A composition for forming a resist underlayer film for lithography including a nitrogen-containing compound having 2 to 6 substituents of the following Formula (1) which bond to nitrogen atoms in one molecule, a polymer, a compound that promotes a crosslinking reaction, and an organic solvent. The nitrogen-containing compound having 2 to 6 substituents of Formula (1) in one molecule is for example a glycoluril derivative of the following Formula (1A).

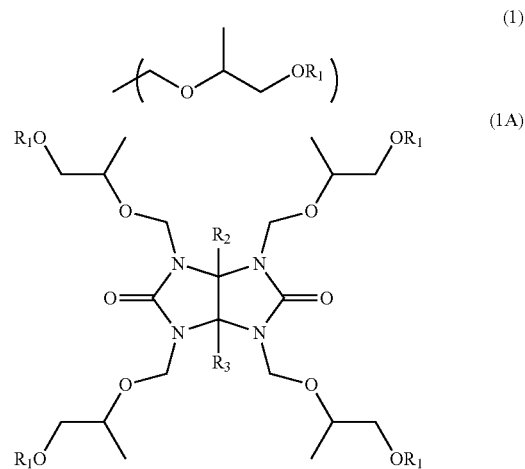

In the formula, each $R_1$ is a methyl group or an ethyl group, and $R_2$ and $R_3$ are independently a hydrogen atom, a $C_{1-4}$ alkyl group, or phenyl group.

8 Claims, 1 Drawing Sheet

COMPOSITION FOR FORMING RESIST UNDERLAYER FILM

TECHNICAL FIELD

The present invention relates to a composition for forming a resist underlayer film for lithography with improved storage stability and a method of producing the same, and a glycoluril derivative included in the composition for forming a resist underlayer film.

BACKGROUND ART

Patent Document 1 discloses a composition for forming a resist underlayer film for lithography, which includes a polymer having a disulfide bond, that is, an "S—S bond" in the main chain, and a solvent, and additionally includes a crosslinkable compound and a sulfonic acid compound.

Patent Document 2 discloses a composition for forming a resist underlayer film which includes (A) a resin, (B) a crosslinking agent having a butyl ether group and (C) a solvent and in which a crosslinking agent having the (B) butyl ether group is a nitrogen-containing cyclic compound having at least two butyl ether groups and the nitrogen-containing cyclic compound is a compound having a glycoluril framework or a triazine framework.

[Patent Document 1] PCT International Publication No. WO 2009/096340

[Patent Document 2] PCT International Publication No. WO 2008/143302

SUMMARY OF THE INVENTION

Problems to be Solved by the Invention

For a composition for forming a resist underlayer film, in addition to stability of the resist underlayer film obtained from the composition, criteria for storage stability to be satisfied for the composition itself have become increasingly strict in recent years. Therefore, further improvement in storage stability of the composition for forming a resist underlayer film is required, and it is required that a peak and the like of a GPC chart of the composition obtained by gel permeation chromatography (hereinafter abbreviated as GPC in this specification) analysis do not change, that is, that a molecular weight distribution do not change even after storage for a long time.

For example, when a nitrogen-containing compound having an alkoxy group and an organic solvent containing alcohols having a hydroxy group are used as a crosslinkable compound and a solvent, respectively, which are components of a composition for forming a resist underlayer film, the alkoxy group and the alcohols having a hydroxy group unintentionally react in the presence of a sulfonic acid compound. As a result, the composition for forming a resist underlayer film has poor storage stability in some cases.

Means for Solving the Problems

An aspect of the present invention is a composition for forming a resist underlayer film for lithography including a nitrogen-containing compound having 2 to 6 substituents of the following Formula (1) which bond to nitrogen atoms in one molecule, a polymer, a compound that promotes a crosslinking reaction, and an organic solvent (in the formula, $R_1$ is methyl group or ethyl group).

The nitrogen-containing compound having 2 to 6 substituents of Formula (1) in one molecule is, for example, a glycoluril derivative of the following Formula (1A)

(in the formula, four $R_1$s are independently methyl group or ethyl group, and $R_2$ and $R_3$ are independently a hydrogen atom, a $C_{1-4}$ alkyl group, or phenyl group).

A second aspect of the present invention is a method of producing the composition for forming a resist underlayer film for lithography according to the first aspect of the present invention including reacting a nitrogen-containing compound having 2 to 6 substituents of the following Formula (2) which bond to nitrogen atoms in one molecule with at least one compound of the following Formula (3) to synthesize a nitrogen-containing compound having 2 to 6 substituents of Formula (1) in one molecule; and dissolving the nitrogen-containing compound having 2 to 6 substituents of Formula (1) in one molecule, the polymer, and a compound that promotes the crosslinking reaction in the organic solvent

(in the formula, $R_1$ is methyl group or ethyl group, and $R_4$ is a $C_{1-4}$ alkyl group).

The nitrogen-containing compound having 2 to 6 substituents of Formula (2) in one molecule is, for example, a glycoluril derivative of the following Formula (2A)

(2A)

(in the formula, $R_2$ and $R_3$ independently are a hydrogen atom, a $C_{1-4}$ alkyl group, or phenyl group, and each $R_4$ is independently a $C_{1-4}$ alkyl group).

A third aspect of the present invention is a glycoluril derivative of the following Formula (1A)

(1A)

(in the formula, four $R_1$s are independently methyl group or ethyl group, and $R_2$ and $R_3$ are independently a hydrogen atom, a $C_{1-4}$ alkyl group, or phenyl group).

A composition for forming a resist underlayer film of the present invention has excellent storage stability at normal temperature (in a range of 20° C.±15° C.). In addition, a resist underlayer film formed of the composition for forming a resist underlayer film of the present invention can be used as an anti-reflective coating, and a desired resist pattern can be formed on the resist underlayer film.

MODES FOR CARRYING OUT THE INVENTION

[Glycoluril Derivative]

Examples of a nitrogen-containing compound having 2 to 6 substituents of Formula (1) in one molecule included in a composition for forming a resist underlayer film of the present invention include a glycoluril derivative of Formula (1A). When $R_2$ and $R_3$ in Formula (1A) are $C_{1-4}$ alkyl group, the alkyl group is not limited to a linear chain and may be a branched chain, and examples thereof include methyl group, ethyl group, n-propyl group, isopropyl group, n-butyl group, isobutyl group and tert-butyl group.

Examples of the glycoluril derivative of Formula (1A) include compounds of the following Formula (1A-1) to Formula (1A-6).

(1A-1)

(1A-2)

(1A-3)

A content of the glycoluril derivative of Formula (1A) is, for example, 1% by mass to 80% by mass, and preferably, 10% by mass to 50% by mass, with respect to a polymer to be described below. A range of a content of a nitrogen-containing compound having 2 to 6 substituents of Formula (1) in one molecule other than the glycoluril derivative of Formula (1A) is the same.

The glycoluril derivative of Formula (1A) is obtained by reacting the glycoluril derivative of Formula (2A) with at least one compound of Formula (3). Examples of the glycoluril derivative of Formula (2A) include compounds of the following Formula (2A-1) to Formula (2A-4). In addition, examples of the compound of Formula (3) include compounds of the following Formula (3-1) and Formula (3-2).

(3-2)

[Melamine Derivative]

In addition, as a nitrogen-containing compound having 2 to 6 substituents of Formula (1) in one molecule included in a composition for forming a resist underlayer film of the present invention, a melamine derivative can be used in place of the glycoluril derivative. Examples of the melamine derivative include compounds of the following Formula (1B-1) and Formula (1B-2).

(1B-1)

(1B-2)

[Polymer]

As a polymer included in the composition for forming a resist underlayer film of the present invention, a polymer used for a composition for forming a resist underlayer film in the related art can be used. When the polymer is a copolymer, any of an alternating copolymer, a block copolymer, and a random copolymer may be used, or any of a copolymer obtained by polymerizing two types of monomers, a terpolymer obtained by polymerizing three types of monomers, and a quaternary copolymer obtained by polymerizing four types of monomers may be used. A repeating structural unit of the polymer included in the composition for forming a resist underlayer film of the present invention will be exemplified in the following Formula (4A) to Formula (4N) and Formula (5A) to Formula (5E), but the repeating structural unit is not limited to such examples.

(4A)

(4B)

-continued (4C)

(4D)

(4E)

(4F)

(4G)

(4H)

-continued

(4I)

(4J)

(4K)

(4L)

(4M)

[Compound that Promotes Crosslinking Reaction]

Examples of a compound that promotes a crosslinking reaction included in the composition for forming a resist underlayer film of the present invention include 4-methylbenzenesulfonic acid, pyridinium p-toluenesulfonate, 4-hydroxybenzenesulfonic acid and 5-sulfosalicylic acid. A content of the compound that promotes the crosslinking reaction is, for example, 0.01% by mass to 15% by mass, with respect to the polymer.

[Organic Solvent]

Examples of the organic solvent included in the composition for forming a resist underlayer film of the present invention include propylene glycol monomethyl ether, propylene glycol monoethyl ether, propylene glycol monopropyl ether, propylene glycol monomethyl ether acetate, methyl ethyl ketone, ethyl lactate, cyclohexanone, γ-butyrolactone, ethyl 3-ethoxypropionate, 4-methyl-2-pentanol, and a mixture of two or more selected from among these organic solvents. A content of the organic solvent included in the composition for forming a resist underlayer film of the present invention is, for example, 40% by mass to 99.9% by mass.

[Other Components]

The composition for forming a resist underlayer film of the present invention may further include a surfactant as an optional component. The surfactant is an additive for improving coating properties for a substrate. A known surfactant such as a nonionic surfactant and a fluorine-based surfactant can be used. A content of the surfactant included in the composition for forming a resist underlayer film of the present invention is, for example, 0.01% by mass to 5% by mass, with respect to the polymer.

The composition for forming a resist underlayer film of the present invention can be applied to a lithography process in a production procedure of a semiconductor device. A resist pattern is formed by performing at least a process of applying the composition for forming a resist underlayer film of the present invention to a semiconductor substrate, performing baking to form a resist underlayer film, a process of forming a resist film on the resist underlayer film, a process of exposing the resist film, a process of developing the resist film using a developer after exposing, and a process of performing a rinse treatment for removing the developer after development.

The exposure is performed using, for example, an ArF excimer laser. EUV (wavelength of 13.5 nm) or an electron beam may be used in place of the ArF excimer laser. "EUV" is an abbreviation for extreme ultraviolet light. The resist for forming a resist film may be either a positive type or a negative type. A chemically amplified resist sensitive to an ArF excimer laser, EUV or an electron beam can be used.

The semiconductor substrate is typically a silicon wafer, and an SOI (Silicon on Insulator) substrate or a compound semiconductor wafer such as gallium arsenide (GaAs), indium phosphide (InP), or gallium phosphide (GaP) may be used. A semiconductor substrate on which an insulating film such as a silicon oxide film, a nitrogen-containing silicon oxide film (SiON film), and a carbon-containing silicon oxide film (SiOC film) is formed may be used. In this case, the composition for forming a resist underlayer film of the present invention is applied to the insulating film.

EXAMPLES

Synthesis examples and examples of the present invention will be described below in detail. However, the present invention is not limited to the following synthesis examples and examples.

An NMR apparatus used for measuring $^1$H NMR in the following Synthesis Example 1 in this specification was a 500 MHz-NMR (JNM-ECA series commercially available from JEOL Ltd.), and a heavy solvent was $CDCl_3$. In addition, weight average molecular weights described in the following Synthesis Example 2 to Synthesis Example 4 were results measured through gel permeation chromatography (hereinafter abbreviated as GPC). For measurement, a GPC apparatus (commercially available from Tosoh Corporation) was used and measurement conditions and the like were as follows.

GPC column: Shodex [registered trademark] Asahipak [registered trademark] (commercially available from Showa Denko K.K.)
Column temperature: 40° C.
Solvent: N,N-dimethylformamide (DMF)
Flow rate: 0.6 mL/min
Standard samples: polystyrene (commercially available from Tosoh Corporation)

Synthesis Example 1

60 g (0.188 mol) of tetramethoxymethylglycoluril (product name: POWDERLINK [registered trademark] 1174 commercially available from Japan Cytec Industries, hereinafter abbreviated as PL-LI in this specification), 1,200 g of propylene glycol monomethyl ether (hereinafter abbreviated as PGME in this specification), and 120 g of a washed ion-exchange resin for a catalyst (product name: AMBERLYST [registered trademark] 15JWET, commercially available from Dow Chemical Company, hereinafter abbreviated as 15JWET in this specification) were put into a 2,000 mL flask, and the mixture was stirred and dissolved at 25° C. and then heated and stirred under a reduced pressure (80 Torr to 100 Torr) at 60° C. for 7 hours. Then, the pressure inside the flask was recovered and cooling was performed to 25° C., and then 15JWET was filtered off to obtain a desired compound (hereinafter abbreviated as PGME-PL in this specification). The obtained compound was identified by $^1$H NMR. As a result, it was confirmed that a peak (31.9 ppm) of a methoxy group of PL-LI disappeared and about 4 molecules of PGME were introduced into one molecule of PL-LI, and the glycoluril derivative of Formula (1A-1) (hereinafter abbreviated as PGME-PL in this specification) was obtained. [1.0 to 1.1 ppm (3H, —$CH_3$), 3.2 to 3.3 ppm (20H, —$OCH_3$ and —$CH_2O$—), 3.6 to 3.8 ppm (4H, —OCH<)]

Reference Example 1

10 g of PGME-PL obtained in Synthesis Example 1 and 0.015 g of 4-methylbenzenesulfonic acid were mixed together, and 50 g of propylene glycol monomethyl ether was added to this mixture, and a solution in which the mixture was dissolved was prepared.

Reference Example 2

10 g of PGME-PL obtained in Synthesis Example 1 and 0.015 g of pyridinium p-toluenesulfonate were mixed together and 50 g of propylene glycol monomethyl ether was added to this mixture, and a solution in which the mixture was dissolved was prepared.

Reference Example 3

10 g of PGME-PL obtained in Synthesis Example 1 and 0.015 g of 4-hydroxybenzenesulfonic acid were mixed together and 50 g of propylene glycol monomethyl ether was added to this mixture, and a solution in which the mixture was dissolved was prepared.

Reference Example 4

10 g of PGME-PL obtained in Synthesis Example 1 and 0.015 g of 5-sulfosalicylic acid were mixed together and 50 g of propylene glycol monomethyl ether was added to this mixture, and a solution in which the mixture was dissolved was prepared.

Comparative Example 1

0.59 g of tetramethoxymethylglycoluril (product name: POWDERLINK [registered trademark] 1174 commercially available from Japan Cytec Industries) and 0.015 g of 4-methylbenzenesulfonic acid were mixed together and 59 g of propylene glycol monomethyl ether was added to this mixture, and a solution in which the mixture was dissolved was prepared.

Comparative Example 2

0.59 g of tetramethoxymethylglycoluril (product name: POWDERLINK [registered trademark] 1174 commercially available from Japan Cytec Industries) and 0.015 g of pyridinium p-toluenesulfonate were mixed together and 59 g of propylene glycol monomethyl ether was added to this mixture, and a solution in which the mixture was dissolved was prepared.

Comparative Example 3

0.59 g of tetramethoxymethylglycoluril (product name: POWDERLINK [registered trademark] 1174 commercially available from Japan Cytec Industries) and 0.015 g of 4-hydroxybenzenesulfonic acid were mixed together and 59 g of propylene glycol monomethyl ether was added to this mixture, and a solution in which the mixture was dissolved was prepared.

Comparative Example 4

0.59 g of tetramethoxymethylglycoluril (product name: POWDERLINK [registered trademark] 1174 commercially available from Japan Cytec Industries) and 0.015 g of 5-sulfosalicylic acid were mixed together and 59 g of propylene glycol monomethyl ether was added to this mixture, and a solution in which the mixture was dissolved was prepared.

It was checked whether an exchange reaction between a crosslinking agent (glycoluril derivative) and propylene glycol monomethyl ether as an organic solvent occurred in the presence of a compound that promoted a crosslinking reaction according to GPC analysis. Regarding solutions prepared in Reference Example 1 to Reference Example 4 and Comparative Example 1 to Comparative Example 4, measurement was performed by GPC immediately after the solutions were prepared, after the solutions were stored at 23° C. for 1 week, and after the solutions were stored at 35° C. for 1 week. In the following Table 1, when there was a change in the GPC chart as compared with immediately after the solution was prepared, this is indicated as "change," whereas, when there was no change, this is indicated as "no change." The result indicates that an exchange reaction between the glycoluril derivative of Formula (1A) and propylene glycol monomethyl ether did not occur, but an exchange reaction between the glycoluril derivative of Formula (2A) and propylene glycol monomethyl ether occurred.

TABLE 1

| | 23° C. for 1 week | 35° C. for 1 week |
|---|---|---|
| Reference Example 1 | No change | No change |
| Reference Example 2 | No change | No change |
| Reference Example 3 | No change | No change |
| Reference Example 4 | No change | No change |
| Comparative Example 1 | Change | Change |
| Comparative Example 2 | Change | Change |
| Comparative Example 3 | Change | Change |
| Comparative Example 4 | Change | Change |

Synthesis Example 2

6.3 g of monoallyl diglycidyl isocyanuric acid (product name: MADGIC commercially available from Shikoku Chemicals Corporation), 5.0 g of 3,3'-dithiodipropionic acid (product name: DTDPA commercially available from Sakai Chemical Industry Co., Ltd.), and 0.20 g of ethyltriphenylphosphonium bromide (commercially available from Tokyo Chemical Industry Co., Ltd.) as a catalyst were added to 45.9 g of propylene glycol monomethyl ether, and dissolution was performed in a reaction container. Air in the reaction container was replaced with nitrogen gas, and then a reaction was caused at 105° C. for 24 hours to obtain a polymer solution. When the obtained polymer solution was subjected to GPC analysis, the weight average molecular weight of the polymer was 4,000 in terms of polystyrene standards.

Synthesis Example 3

10.0 g of monomethyl diglycidyl isocyanuric acid (product name: MeDGIC commercially available from Shikoku Chemicals Corporation), 4.4 g of 3,3'-dithiodipropionic acid (product name: DTDPA commercially available from Sakai Chemical Industry Co., Ltd.), and 0.37 g of ethyltriphenylphosphonium bromide (commercially available from Tokyo Chemical Industry Co., Ltd.) as a catalyst were added to 33.37 g of propylene glycol monomethyl ether, and dissolution was performed in a reaction container. Air in the reaction container was replaced with nitrogen gas, and then a reaction was caused at 105° C. for 24 hours to obtain a polymer solution. When the obtained polymer solution was subjected to GPC analysis, the weight average molecular weight of the polymer was 3,000 in terms of polystyrene standards.

Synthesis Example 4

10 g of benzyl methacrylate (commercially available from Tokyo Chemical Industry Co., Ltd.), 19.2 g of hydroxypropyl methacrylate (commercially available from Tokyo Chemical Industry Co., Ltd.), and 10.8 g of γ-butyrolactone methacrylate (commercially available from Osaka Organic Chemical Industry Ltd.) were dissolved in 128 g of propylene glycol monomethyl ether. Then, air in a flask was replaced with nitrogen gas and the temperature was raised to 80° C. Then, 1.6 g of methyl 2,2'-azobisisobutyrate was dissolved in 30.4 g of propylene glycol monomethyl ether, added under a nitrogen pressure, and a reaction was caused at 80° C. for 24 hours to obtain a polymer. The weight average molecular weight of the obtained polymer (resin) was 10,000 in terms of polystyrene.

Example 1

A composition for forming a resist underlayer film for lithography was prepared, in which 7.09 g of the polymer solution obtained in Synthesis Example 2 was mixed with 5.95 g of PGME-PL obtained in Synthesis Example 1 and 0.03 g of 4-hydroxybenzenesulfonic acid, 122.08 g of propylene glycol monomethyl ether and 14.85 g of propylene glycol monomethyl ether acetate were added to this mixture, and the mixture was dissolved.

Example 2

A composition for forming a resist underlayer film for lithography was prepared, in which 1.25 g of the polymer solution obtained in Synthesis Example 3 was mixed with 0.97 g of PGME-PL obtained in Synthesis Example 1 and 0.01 g of 5-sulfosalicylic acid, 24.80 g of propylene glycol monomethyl ether and 2.97 g of propylene glycol monomethyl ether acetate were added to this mixture, and the mixture was dissolved.

Example 3

A composition for forming a resist underlayer film for lithography was prepared, in which 17.17 g of the polymer solution obtained in Synthesis Example 4 was mixed with 17.02 g of PGME-PL obtained in Synthesis Example 1 and 0.05 g of pyridinium p-toluenesulfonate, 101.19 g of propylene glycol monomethyl ether and 14.57 g of propylene glycol monomethyl ether acetate were added to this mixture, and the mixture was dissolved.

Comparative Example 5

A composition for forming a resist underlayer film for lithography was obtained, in which 7.09 g of the polymer solution obtained in Synthesis Example 2 was mixed with 0.29 g of tetramethoxymethylglycoluril (product name: POWDERLINK [registered trademark] 1174 commercially available from Japan Cytec Industries) and 0.03 g of 4-hydroxybenzenesulfonic acid, 124.82 g of propylene glycol monomethyl ether and 14.85 g of propylene glycol monomethyl ether acetate were added to this mixture, and the mixture was dissolved.

Comparative Example 6

A composition for forming a resist underlayer film for lithography was obtained, in which 1.25 g of the polymer solution obtained in Synthesis Example 3 was mixed with 0.05 g of tetramethoxymethylglycoluril (product name: POWDERLINK [registered trademark] 1174 commercially available from Japan Cytec Industries) and 0.01 g of 5-sulfosalicylic acid, 25.12 g of propylene glycol monomethyl ether and 2.97 g of propylene glycol monomethyl ether acetate were added to this mixture, and the mixture was dissolved.

Comparative Example 7

A composition for forming a resist underlayer film for lithography was obtained, in which 7.09 g of the polymer solution obtained in Synthesis Example 4 was mixed with 0.29 g of tetramethoxymethylglycoluril (product name: POWDERLINK [registered trademark] 1174 commercially available from Japan Cytec Industries) and 0.03 g of 4-hydroxybenzenesulfonic acid, 124.82 g of propylene glycol monomethyl ether and 14.85 g of propylene glycol monomethyl ether acetate were added to this mixture, and the mixture was dissolved.

Regarding solutions prepared in Example 1 to Example 3 and Comparative Example 5 to Comparative Example 7, measurement was performed by GPC immediately after the solutions were prepared, after the solutions were stored at 23° C. for 1 week, and after the solutions were stored at 35° C. for 1 week. In the following Table 2, when there was an obvious change in the GPC chart as compared with immediately after the solution was prepared, this is indicated as "change," whereas, when there was hardly any change, this is indicated as "no change." The results indicate that the composition for forming a resist underlayer film of the present invention had excellent storage stability, but a composition for forming a resist underlayer film including the glycoluril derivative of Formula (2A) had poor storage stability

TABLE 2

|  | 23° C. for 1 week | 35° C. for 1 week |
|---|---|---|
| Example 1 | No change | No change |
| Example 2 | No change | No change |
| Example 3 | No change | No change |
| Comparative Example 1 | Change | Change |
| Comparative Example 2 | Change | Change |
| Comparative Example 3 | Change | Change |

[Measurement of Optical Parameters]

The compositions for forming a resist underlayer film prepared in Example 1 to Example 3 and Comparative Example 5 to Comparative Example 7 were applied to silicon wafers by a spinner. The silicon wafers to which the compositions for forming a resist underlayer film were applied were baked on a hot plate at 205° C. for 1 minute to form resist underlayer films. An n value (refractive index) and a k value (a damping coefficient or an absorption coefficient) at a wavelength of 193 nm of these six types of resist underlayer films were measured using a spectroscopic ellipsometer (VUV-VASE VU-302 commercially available from J. A. Woollam). The results are shown in the following Table 3. It shows that all of the resist underlayer films had an effective n value and k value with respect to a wavelength of 193 nm and the effect of an anti-reflective coating was obtained. In addition, comparing Example 1 and Comparative Example 5, the results showed that the resist underlayer films had almost no change in the n value and the k value. Similarly, comparing Example 2 and Comparative Example 6, and comparing Example 3 and Comparative Example 7, the results showed that the resist underlayer films had almost no change in the n value and the k value.

[Measurement of Contact Angle]

The compositions for forming a resist underlayer film prepared in Example 1 to Example 3 and Comparative Example 5 to Comparative Example 7 were applied to silicon wafers by a spinner. The silicon wafers to which the compositions for forming a resist underlayer film were applied were baked on a hot plate at 205° C. for 1 minute to form resist underlayer films. Then, using water and diiodomethane as a liquid sample, contact angles of surfaces of six types of resist underlayer films formed were measured using a DropMaster700 (commercially available from Kyowa Interface Science Co., Ltd.). The results are shown in the following Table 3. It shows that the surfaces of all of the resist underlayer films had favorable wettability (lyophilicity) with respect to water and diiodomethane. In addition, comparing Example 1 and Comparative Example 5, the results showed that the contact angles of the surfaces of the resist underlayer films with respect to water and diiodomethane had almost no change. Similarly, comparing Example 2 and Comparative Example 6 and comparing Example 3 and Comparative Example 7, the results showed that the contact angles of the surfaces of the resist underlayer films with respect to water and diiodomethane had almost no change.

TABLE 3

|  | n value/k value (193 nm) | Contact angle water/diiodomethane |
| --- | --- | --- |
| Example 1 | 1.95/0.28 | 51°/26° |
| Example 2 | 1.95/0.26 | 47°/19° |
| Example 3 | 1.82/0.25 | 60°/31° |
| Comparative Example 5 | 1.96/0.28 | 52°/28° |
| Comparative Example 6 | 1.95/0.25 | 47°/19° |
| Comparative Example 7 | 1.82/0.24 | 62°/31° |

[Formation and Evaluation of Resist Pattern]

Figure 1:
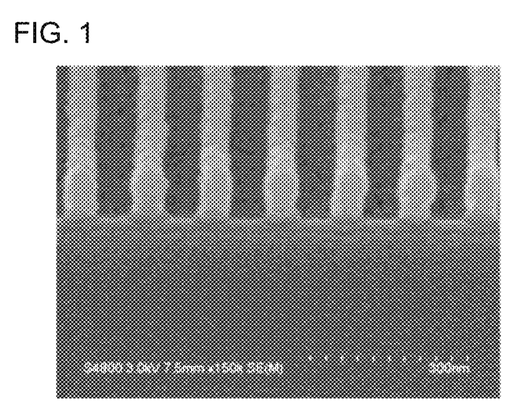
FIG. 1 is a sectional SEM image showing a result obtained by forming a resist pattern on a resist underlayer film formed on a substrate using a composition for forming a resist underlayer film prepared in Example 1.
Figure 2:
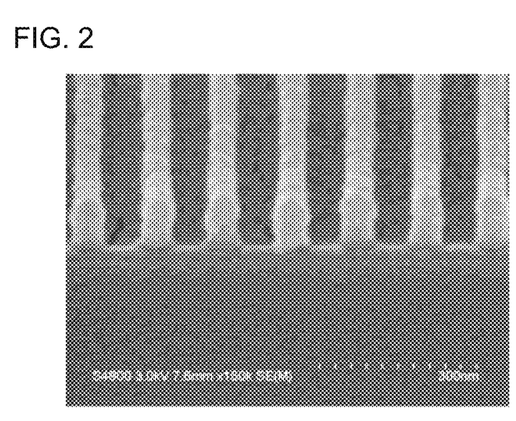
FIG. 2 is a sectional SEM image showing a result obtained by forming a resist pattern on a resist underlayer film formed on a substrate using a composition for forming a resist underlayer film prepared in Example 2.
Figure 3:
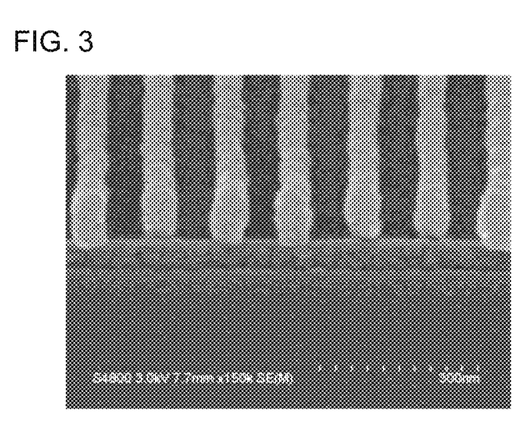
FIG. 3 is a sectional SEM image showing a result obtained by forming a resist pattern on a resist underlayer film formed on a substrate using a composition for forming a resist underlayer film prepared in Example 3.

The compositions for forming a resist underlayer film prepared in Example 1 to Example 3 were applied by a spinner to substrates in which a SiON film (nitrogen-containing silicon oxide film) was formed in a thickness of 0.05 μm on a silicon wafer. Subsequently, the substrates to which the compositions for forming a resist underlayer film were applied were baked on a hot plate at 205° C. for 1 minute and resist underlayer films with a film thickness of 20 nm to 30 nm were formed. A commercially available photoresist solution (product name: PAR855 commercially available from Sumitomo Chemical Company, Ltd.) was applied to these six types of resist underlayer films by a spinner, baking was performed on a hot plate at 105° C. for 1 minute, and photoresist films were formed. Next, using a scanner [NSRS307E (wavelength of 193 nm, NA: 0.85) commercially available from Nikon Corporation], after development, the photoresist films were exposed through a photomask set to have a pattern in which a line width of a photoresist and a width between lines of the photoresist were set to 0.065 μm, that is, 0.065 μmL/S. Then, post exposure baking (PEB) was performed on a hot plate at 100° C. for 60 seconds. After cooling, a 0.26 normal tetraethylammonium hydroxide aqueous solution was used as a developer for development, and additionally a rinse treatment was performed. Through the above procedures, a resist pattern was formed. A cross section of the obtained resist pattern in a direction perpendicular to the substrate was observed under a scanning electron microscope (SEM) and it was confirmed that a desired resist pattern was formed. The results are shown in FIG. 1 to FIG. 3.

The invention claimed is:

1. A composition for forming a resist underlayer film for lithography including a nitrogen-containing compound having 2 to 6 substituents of the following Formula (1) which bond to nitrogen atoms in one molecule, a polymer, a compound that promotes a crosslinking reaction, and an organic solvent (1)

in the formula, $R_1$ is a methyl group or an ethyl group.

2. The composition for forming a resist underlayer film for lithography according to claim 1, wherein the nitrogen-containing compound having 2 to 6 substituents of Formula (1) in one molecule is a glycoluril derivative of the following Formula (1A)

(1A)

in the formula, four $R_1$s are independently methyl group or ethyl group, and $R_2$ and $R_3$ are independently a hydrogen atom, a $C_{1-4}$ alkyl group, or phenyl group.

3. The composition for forming a resist underlayer film for lithography according to claim 1, wherein the organic solvent is one selected from the group consisting of propylene glycol monomethyl ether, propylene glycol monoethyl ether, propylene glycol monopropyl ether, propylene glycol monomethyl ether acetate, methyl ethyl ketone, ethyl lactate, cyclohexanone, γ-butyrolactone, ethyl 3-ethoxypropionate, and 4-methyl-2-pentanol, or a mixture of two or more thereof.

4. The composition for forming a resist underlayer film for lithography according to claim 1, wherein a content of the nitrogen-containing compound having 2 to 6 substituents of Formula (1) in one molecule is 1% by mass to 80% by mass with respect to the polymer.

5. The composition for forming a resist underlayer film for lithography according to claim 1, wherein the compound that promotes a crosslinking reaction is selected from 4-methylbenzenesulfonic acid, pyridinium p-toluenesulfonate, 4-hydroxybenzenesulfonic acid or 5-sulfosalicylic acid.

6. A method of producing the composition for forming a resist underlayer film for lithography according to claim 1, the method comprising reacting a nitrogen-containing compound having 2 to 6 substituents of the following Formula (2) which bond to nitrogen atoms in one molecule with at least one compound of the following Formula (3) to synthesize a nitrogen-containing compound having 2 to 6 substituents of Formula (1) in one molecule; and dissolving the nitrogen-containing compound having 2 to 6 substituents of Formula (1) in one molecule, the polymer, and a compound that promotes the crosslinking reaction in the organic solvent (2)

(3)

in the formula, $R_1$ is methyl group or ethyl group, and $R_4$ is a $C_{1-4}$ alkyl group.

7. The method of producing the composition for forming a resist underlayer film for lithography according to claim 6, wherein the nitrogen-containing compound having 2 to 6 substituents of Formula (2) in one molecule is a glycoluril derivative of the following Formula (2A)

(2A)

in the formula, $R_2$ and $R_3$ independently are a hydrogen atom, a $C_{1-4}$ alkyl group, or phenyl group, and each $R_4$ is independently a $C_{1-4}$ alkyl group.

8. A glycoluril derivative of the following Formula (1A)

(1A)

in the formula, the four $R_1$s are independently methyl group or ethyl group, and $R_2$ and $R_3$ are independently a hydrogen atom, a $C_{1-4}$ alkyl group, or phenyl group, with the proviso that the gylcoluril derivative in which each of the $R_1$s is methyl and each of $R_2$ and $R_3$ is a hydrogen atom is excluded.

* * * * *